(12) United States Patent  
Asai

(10) Patent No.: US 11,548,847 B2  
(45) Date of Patent: Jan. 10, 2023

(54) AMINE COMPOSITION, AMINE COMPOUND, PRODUCTION METHOD, AND APPLICATION THEREOF

(71) Applicant: MITSUBISHI GAS CHEMICAL COMPANY, INC., Tokyo (JP)

(72) Inventor: Yuiga Asai, Tokyo (JP)

(73) Assignee: MITSUBISHI GAS CHEMICAL COMPANY, INC., Tokyo (JP)

(*) Notice: Subject to any disclaimer, the term of this patent is extended or adjusted under 35 U.S.C. 154(b) by 0 days.

(21) Appl. No.: 17/433,134

(22) PCT Filed: Feb. 21, 2020

(86) PCT No.: PCT/JP2020/007130  
§ 371 (c)(1),  
(2) Date: Aug. 23, 2021

(87) PCT Pub. No.: WO2020/175380  
PCT Pub. Date: Sep. 3, 2020

(65) Prior Publication Data  
US 2022/0194892 A1 Jun. 23, 2022

(30) Foreign Application Priority Data  
Feb. 26, 2019 (JP) .............................. JP2019-032383

(51) Int. Cl.  
C07C 211/27 (2006.01)  
C08G 18/32 (2006.01)  
C08G 59/50 (2006.01)

(52) U.S. Cl.  
CPC ........ C07C 211/27 (2013.01); C08G 18/3234 (2013.01); C08G 59/5033 (2013.01)

(58) Field of Classification Search  
CPC .............. C07C 211/27; C08G 18/3234; C08G 59/5033  
USPC ....................................................... 514/649  
See application file for complete search history.

(56) References Cited

U.S. PATENT DOCUMENTS

| | | |
|---|---|---|
| 4,506,099 A | 3/1985 | Baumeister et al. |
| 5,587,388 A | 12/1996 | Kim et al. |
| 2005/0159626 A1 | 7/2005 | Allgeier et al. |
| 2013/0303805 A1 | 11/2013 | Kuwahara et al. |
| 2017/0355808 A1 | 12/2017 | Langkabel et al. |
| 2019/0112416 A1 | 4/2019 | Sato et al. |

FOREIGN PATENT DOCUMENTS

| | | |
|---|---|---|
| CN | 103339099 A | 10/2013 |
| CN | 107428675 A | 12/2017 |
| CN | 109071412 A | 12/2018 |
| EP | 2 671 865 A1 | 12/2013 |
| EP | 3 441 385 A1 | 2/2019 |
| JP | H7-2820 A | 1/1995 |
| JP | 2016-536287 A | 11/2016 |
| JP | 2018-024835 A | 2/2018 |
| WO | WO 2012/105303 A1 | 8/2012 |
| WO | WO 2015/069531 A1 | 5/2015 |
| WO | WO 2017/175740 A1 | 10/2017 |

OTHER PUBLICATIONS

Office Action for CN App. No. 202080016369.5, dated Dec. 22, 2021.  
Cookson et al., "Photochemical Addition of Amines to Styrenes", Chemical Communications, pp. 753-754 (1969).  
ISR for PCT/JP2020/007130, dated May 19, 2020.  
IPRP for PCT/JP2020/007130, dated Aug. 25, 2021.  
Supplementary ESR for EP App. No. 20 76 2444.6, dated Mar. 23, 2022.  
Database Registry [Online], Chemical Abstracts Service, Columbus, OH; Apr. 25, 2016; XP055898670, retrieved from STN Database accession No. 1896848-42-2; compounds with CAS Registry Nos. 1896848-42-2, 1896847-93-0, 1896847-72-5.  
Database Registry [Online], Chemical Abstracts Service, Columbus, OH; Apr. 24, 2016; XP055898673, retrieved from STN Database accession No. 1896614-45-1; compounds with CAS Registry Nos. 1896614-45-1, 1896613-94-7, 1896250-23-9, 1896249-38-9, 1896247-53-2.  
Database Registry [Online], Chemical Abstracts Service, Columbus, OH; Apr. 22, 2016; XP055898674, retrieved from STN Database accession No. 1895383-79-5; compounds with CAS Registry Nos. 1895383-79-5, 1895145-18-2.

(Continued)

*Primary Examiner* — Kristin A Vajda  
(74) *Attorney, Agent, or Firm* — Greenblum & Bernstein, P.L.C.

(57) ABSTRACT

Provided are a novel amine composition and a novel amine compound. Also provided are a method for producing the amine composition and amine compound, and an epoxy resin curing agent, an epoxy resin composition, a cured product, a urethane prepolymer curing agent, a polyurethane urea resin composition, a polyamide varnish, and a polyamide, each obtained using the amine composition and amine compound. The amine composition contains a compound represented by Formula (1), wherein A is a cyclic alkylene group, and B is a group containing an aryl group or a heteroaryl group.

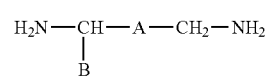

(1)

20 Claims, No Drawings

(56) References Cited

OTHER PUBLICATIONS

Database Registry [Online], Chemical Abstracts Service, Columbus, OH; Apr. 21, 2016; XP055898676, retrieved from STN Database accession No. 1895022-94-2; compounds with CAS Registry Nos. 1895022-94-2,1895022-36-2, 1894707-94-8, 1894705-81-7, 1894705-66-8.
Database Registry [Online], Chemical Abstracts Service, Columbus, OH; Apr. 20, 2016; XP055898681, retrieved from STN Database accession No. 1893949-09-1; compounds with CAS Registry Nos. 1893949-09-1, 1893948-98-5, 1893948-90-7, 1893477-70-7.
Database Registry [Online], Chemical Abstracts Service, Columbus, OH; Apr. 18, 2016; XP055898683, retrieved from STN Database accession No. 1892354-30-1; compounds with CAS Registry Nos. 1892354-30-1, 1892354-03-8.
Database Registry [Online], Chemical Abstracts Service, Columbus, OH; Apr. 15, 2016; XP055898685, retrieved from STN Database accession No. 1890626-06-8; compounds with CAS Registry Nos. 1890626-06-8, 1890609-33-2, 1890609-25-2, 1890608-10-2.
Database Registry [Online], Chemical Abstracts Service, Columbus, OH; Apr. 14, 2016; XP055898688, retrieved from STN Database accession No. 1890213-31-6; compounds with CAS Registry Nos. 1890213-31-6, 1890073-18-3, 1890035-55-8.

AMINE COMPOSITION, AMINE COMPOUND, PRODUCTION METHOD, AND APPLICATION THEREOF

TECHNICAL FIELD

The present invention relates to a novel amine composition and a novel amine compound. The present invention also relates to a method for producing the amine composition and the amine compound, and to an epoxy resin curing agent, an epoxy resin composition, a cured product, a urethane prepolymer curing agent, a polyurethane urea resin composition, a polyamide varnish, and a polyamide, each obtained using the amine composition or amine compound.

BACKGROUND ART

An amine compound containing an amino group as a functional group is useful as a curing agent for various resins including epoxy resins (for example, refer to Patent Documents 1 to 4). Amine compounds are also used as a synthetic raw material for a polyamide or polyurea, and are widely used as a coating material or a material for a molded product.

CITATION LIST

Patent Documents

Patent Document 1: JP 2018-024835 A
Patent Document 2: JP 2016-536287 T
Patent Document 3: WO 2017/175740
Patent Document 4: WO 2012/105303

SUMMARY OF INVENTION

Technical Problem

In addition to the various applications described above, amine compounds and compositions containing the same are widely subject to research and development, and improvements in various properties have advanced. On the other hand, in view of technological progress and the expansion of applications in various fields in recent years, a demand now exists to further expand material options.

Therefore, an object of the present invention is to provide a novel amine composition, an amine compound contained therein, a method for manufacturing the amine composition and the amine compound, an epoxy resin curing agent using the amine composition or amine compound, an epoxy resin composition, a cured product thereof, a polyurethane prepolymer curing agent, a polyurethane urea resin composition, a cured product thereof, a polyamide varnish, and a polyamide.

Solution to Problem

In consideration of the above problem, the inventors carried on with research and development regarding the synthesis of novel amine compounds, and as a result, successfully synthesized novel amine compounds having a cyclic alkylene group (preferably a norbornane diyl group). The present invention solves the problem described above based on synthesis of such novel compounds, and in particular, the problem is solved by the following aspects.

<1> An amine composition containing a compound represented by Formula (1).

[Chem. 1]

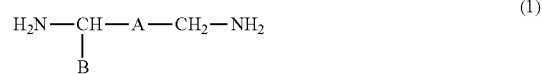

(In Formula (1), A is a cyclic alkylene group, and B is a group containing an aryl group or a heteroaryl group.)

<2> The amine composition according to <1>, wherein A in Formula (1) is a norbornane diyl group.

<3> The amine composition according to <1> or <2>, wherein B in Formula (1) is a group containing a phenyl group.

<4> The amine composition according to any one of <1> to <3>, further including a compound represented by Formula (2).

[Chem. 2]

(In Formula (2), E is a group containing an aryl group or a heteroaryl group.)

<5> The amine composition according to <4>, wherein E in Formula (2) is a group containing a phenyl group.

<6> The amine composition according to any one of <1> to <5>, wherein the aryl or heteroaryl group, which is B in Formula (1), is bonded to a methine group (CH) in Formula (1) without a linking group being interposed therebetween.

<7> A method for producing an amine compound represented by Formula (1) or an amine composition containing the compound represented by Formula (1), the method including:

reacting a compound represented by Formula (2) with a compound represented by Formula (3) in the presence of a base composition.

[Chem. 3]

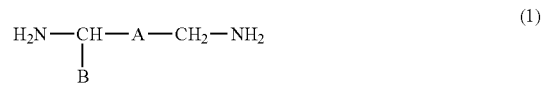

(In Formula (1), A is a cyclic alkylene group, and B is a group containing an aryl group or a heteroaryl group.)

[Chem. 4]

(In Formula (2), E is a group containing an aryl group or a heteroaryl group.)

[Chem. 5]

(In Formula (3), D is a cyclic alkenyl group.)

<8> The production method according to <7>, wherein the base composition includes: a cesium-containing compound (a) selected from cesium carbonate and cesium hydroxide; and a metallic sodium (b).

<9> The production method according to <7> or <8>, wherein, in the reaction between the compound represented by Formula (2) and the compound represented by Formula (3), the base composition added in fractions two or more times.

<10> An amine compound represented by Formula (1).

[Chem. 6]

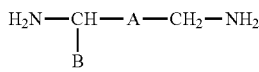
(1)

(In Formula (1), A is a cyclic alkylene group, and B is a group containing an aryl group or a heteroaryl group.)

<11> The amine compound according to <10>, wherein A in Formula (1) is a norbornane diyl group.

<12> The amine compound according to <10> or <11>, wherein B in Formula (1) is a group containing a phenyl group.

<13> The amine compound according to any one of <10> to <12>, wherein the aryl or heteroaryl group, which is B in Formula (1), is bonded to a methine group (CH) in Formula (1) without a linking group being interposed therebetween.

<14> An epoxy resin curing agent containing an amine composition described in any one of <1> to <6> or an amine compound described in any one of <10> to <13>.

<15> An epoxy resin composition containing the epoxy resin curing agent described in <14> and an epoxy resin.

<16> A cured product formed from the epoxy resin composition described in <15>.

<17> A urethane prepolymer curing agent containing an amine composition described in any one of <1> to <6> or an amine compound described in any one of <10> to <13>.

<18> A polyurethane urea resin composition containing the urethane prepolymer curing agent described in <17> and a urethane prepolymer.

<19> A cured product formed from the polyurethane urea resin composition described in <18>.

<20> A polyamide varnish containing an amine composition described in any one of <1> to <6> or an amine compound described in any one of <10> to <13> and a compound containing at least one carboxyl group.

<21> A polyamide that is a polycondensate of the polyamide varnish described in <20>.

Advantageous Effects of Invention

According to the present invention, a novel amine compound, an amine composition containing the same, and a method for producing these, an epoxy resin curing agent using the amine composition or the amine compound, an epoxy resin composition, a cured product thereof, a polyurethane prepolymer curing agent, a polyurethane urea resin composition, a cured product thereof, a polyamide varnish, and a polyamide can be provided.

DESCRIPTION OF EMBODIMENTS

The contents of the present invention will be described in detail below. In the present specification, "from . . . to . . . " or "of . . . to . . . " is used to mean that the numerical values described before and after "to" are included as the lower limit and the upper limit, respectively.

<Amine Composition and Amine Compound>

An amine composition according to the present embodiment includes a compound represented by Formula (1).

[Chem. 7]

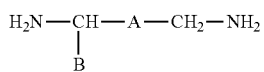
(1)

(In Formula (1), A is a cyclic alkylene group, and B is a group containing an aryl group or a heteroaryl group.)

In Formula (1), A is a cyclic alkylene group. That is, the cyclic alkylene group is directly bonded to the methine group (CH) and the methylene group ($CH_2$) in the formula.

The cyclic alkylene group herein may have a substituent. However, the cyclic alkylene group is preferably unsubstituted.

The cyclic alkylene group is preferably a cyclic alkylene group having from 3 to 10 carbons, and is more preferably a cyclic alkylene group having from 5 to 8 carbons. In addition, the cyclic alkylene group is preferably one having a crosslinking structure.

Specific examples of A include a cyclobutane diyl group, a cyclopentane diyl group, a cyclohexane diyl group, a norbornane diyl group, and a cyclooctane diyl group, and among these, a norbornane diyl group is particularly preferable. The norbornane diyl group is preferably a group represented by Formula (N1) or (N2). In the formulas, * represents a bond position.

[Chem. 8]

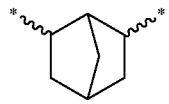
(N1)

(N2)

In Formula (1), B is a group containing an aryl group or a heteroaryl group, and is preferably a group containing an aryl group.

The aryl group or heteroaryl group herein may have a substituent such as an aminomethyl group or may be substituted with a methine group (CH) in the formula through a linking group. However, the aryl group or heteroaryl group is preferably unsubstituted. Also, the aryl group or heteroaryl group is preferably bonded to the methine group (CH) in the formula without interposing a linking group.

Note that in the present specification, "aryl group" means a substituted or unsubstituted aromatic hydrocarbon group, and means that a "heteroaryl group" is not included.

The aryl group is preferably one having from 6 to 22 carbons, more preferably from 6 to 18 carbons, and even more preferably from 6 to 10 carbons. Specific examples of the aryl group include a phenyl group, naphthyl group, anthracenyl group, phenanthrenyl group, biphenylyl group, and fluorenyl group, among which a phenyl group is preferable.

The heteroaryl group is preferably one having from 1 to 24 carbons, more preferably from 2 to 12 carbons, and even more preferably from 3 to 6 carbons. Specific examples of the heteroaryl group include a thienyl group, furyl group, pyridyl group, oxazolyl group, pyrrolyl group, imidazolyl group, pyrazolyl group, indolyl group, and triazinyl group.

The molecular weight of the compound represented by Formula (1) is preferably not less than 150, more preferably not less than 180, and even more preferably not less than 200. The upper limit is preferably not greater than 800, more preferably not greater than 500, and even more preferably not greater than 300.

In the amine composition according to the present embodiment, a content of the amine compound represented by Formula (1) is not particularly limited, but when the composition is produced at a high concentration by distillation or the like, the concentration of the compound represented by Formula (1) above is preferably not less than 70 mass %, more preferably not less than 80 mass %, and even more preferably not less than 90 mass %. An upper limit does not particularly exist, and the composition may have a concentration of 100 mass % of the compound represented by Formula (1) above.

The amine composition according to the present embodiment may further contain a compound represented by Formula (2).

[Chem. 9]

$H_2N-CH_2-E$  (2)

(In Formula (2), E is a group containing an aryl group or a heteroaryl group.)

In Formula (2), E is a group containing an aryl group or a heteroaryl group, and is preferably a group containing an aryl group.

E is synonymous with B in Formula (1), and the preferred range is also the same.

Examples of the compound represented by Formula (2) include benzylamine.

The molecular weight of the compound represented by Formula (2) is preferably not less than 80, more preferably not less than 90, and even more preferably not less than 100. The upper limit is preferably not greater than 500, more preferably not greater than 300, and even more preferably not greater than 200.

In the amine composition according to the present embodiment, a content of the compound represented by Formula (2) is not particularly limited, but when the purity of the compound represented by Formula (1) is increased through distillation purification or the like, the amine composition may substantially not contain the compound represented by Formula (2). The content of the compound represented by Formula (2) is preferably not greater than 1 mass %, more preferably not greater than 0.5 mass %, and even more preferably not greater than 0.1 mass %. The lower limit is not particularly limited, but from a practical perspective, the content is not less than 0.001 mass %.

The amine composition according to the present embodiment may further contain a compound represented by Formula (3).

[Chem. 10]

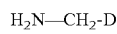

$H_2N-CH_2-D$  (3)

(In Formula (3), D is a cyclic alkenyl group.)

In Formula (3), D is a cyclic alkenyl group. That is, the cyclic alkenyl group is substituted at (directly bonded to) the methylene group ($CH_2$) in the formula without interposing a linking group.

The cyclic alkenyl group may have a substituent. However, the cyclic alkenyl group is preferably unsubstituted.

Here, the cyclic alkenyl group is preferably a cyclic alkylene group having from 3 to 10 carbons, and is more preferably a cyclic alkylene group having from 5 to 8 carbons. In addition, the cyclic alkenyl group is preferably a cyclic alkylene group having a crosslinking structure.

The number of double bonds included in the cyclic alkenyl group is preferably one or two, and more preferably one. Specific examples of D include a cyclobutenyl group, cyclopentenyl group, cyclohexenyl group, norbornenyl group, and cyclooctenyl group, and of these, a norbornenyl group is particularly preferable. The norbornenyl group is preferably a group represented by Formula (N3) or (N4). In the formulas, * represents a bond position.

[Chem. 11]

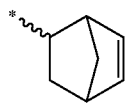

(N3)

(N4)

The molecular weight of the compound represented by Formula (3) is preferably not less than 90, more preferably not less than 100, and even more preferably not less than 110. The upper limit is preferably not greater than 600, more preferably not greater than 400, and even more preferably not greater than 300.

In the amine composition according to the present embodiment, a content of the compound represented by Formula (3) is not particularly limited, but when the purity of the compound represented by Formula (1) is increased through distillation purification or the like, the amine composition may substantially not contain the compound represented by Formula (3). The content of the compound represented by Formula (3) is preferably not greater than 1 mass %, more preferably not greater than 0.5 mass %, and even more preferably not greater than 0.1 mass %. The lower limit is not particularly limited, but from a practical perspective, the content is not less than 0.001 mass %.

In the synthesis reaction of the present invention, amines and an alkali metal may be used simultaneously, and it is possible that a certain compound may be included as a byproduct, where the certain compound is formed by a reduction, through a Benkeser reduction, of an aromatic ring of an aryl group or heteroaryl group in the compound represented by Formula (1) or the compound represented by Formula (2) to, for example, a 1,3-cyclohexadiene ring or a 1,4-cyclohexadiene rings. In addition, in this reaction, a deammoniation or dehydrogenation type condensation reaction occurs between two amino groups in the compounds of Formulas (1) to (3), and it is possible that an imine compound or an α,β-diamino compound may be included as a byproduct.

<Method for Producing an Amine Compound and an Amine Composition>

The compound represented by Formula (1) and the amine composition are produced by reacting a compound represented by Formula (2) and a compound represented by Formula (3) in the presence of a base composition. One type of each of the compound represented by Formula (2) and the compound represented by Formula (3) may be used alone, or two or more types of each may be used. When two or more types are used, the total amount is preferably in the above range.

A molar ratio of the compound represented by Formula (2) to the compound represented by Formula (3), (Formula (2)/Formula (3)), is preferably not less than 0.2 times, more preferably not less than 0.4 times, even more preferably not less than 0.8 times, and yet even more preferably not less than 1.6 times. Furthermore, the upper limit value of the molar ratio of the compound represented by Formula (2) to the compound represented by Formula (3)), (Formula (2)/Formula (3)), is preferably not greater than 5.0 times, and more preferably not greater than 2.5 times.

«Base Composition»

An example of the base composition is a base composition containing at least one type of an alkali metal-containing compound (a) (compound containing a periodic table group 1 element) and a metallic sodium (b). A preferable example is a composition containing at least one type of an alkali metal-containing compound (a) (compound containing a periodic table group 1 element), at least one type of an alkaline earth metal-containing compound (c) (compound containing a periodic table group 2 element), and a metallic sodium (b). When the base composition contains an alkaline earth metal-containing compound (c), stickiness of the base composition can be suppressed, and handling ease can be improved.

Examples of the alkali metal-containing compound (a) include a potassium-containing compound, a rubidium-containing compound, a cesium-containing compound, and a francium-containing compound. A potassium-containing compound or cesium-containing compound is preferable, and a cesium-containing compound is more preferable. The alkali metal-containing compound (a) is preferably $M^aOH$ or $M^a_2CO_3$ (where $M^a$ is an alkali metal).

The alkaline earth metal-containing compound (c) is preferably a calcium-containing compound or a magnesium-containing compound, and is more preferably a magnesium-containing compound. The alkaline earth metal-containing compound (c) is preferably $M^c(OH)_2$, or $M^cCO_3$, $M^cO$ (where $M^c$ is an alkaline earth metal).

Specific examples of the base composition used in the present invention include compositions containing a metallic sodium and a cesium-containing compound selected from cesium carbonate and cesium hydroxide. Another example is the composition described in JP H10-259147 A.

One type of the alkali metal-containing compound (a) may be used alone, or a combination of two or more types may be used.

From the perspective of efficient progress of the reaction, in the base composition, a molar ratio of the substance amount of the alkali metal included in the alkali metal-containing compound (a) to the substance amount of the metallic sodium (b) ((substance amount of alkali metal): (substance amount of sodium)) is from 0.50:1 to 8.0:1, preferably from 1.0:1 to 4.0:1, more preferably from 1.0:1 to 3.0:1, and even more preferably from 1.5:1 to 2.5:1.

When a total amount of the alkali metal-containing compound (a) and the metallic sodium (b) is defined as 100 parts by mass, a content of the alkaline earth metal-containing compound (c) in the base composition is preferably from 30 to 150 parts by mass, more preferably from 40 to 130 parts by mass, and even more preferably from 50 to 100 parts by mass. When the content of the alkaline earth metal-containing compound (c) is not less than 30 parts by mass, stickiness of the base composition tends to be suppressed. In addition, when the content of the alkaline earth metal-containing compound (c) is not greater than 150 parts by mass, the reaction readily proceeds without affecting an activity of the base composition as a catalyst.

One type of the alkaline earth metal-containing compound (c) may be used alone, or a combination of two or more types may be used.

The base composition can be produced by thermal treatment of a mixture containing the alkali metal-containing compound (a) and the metallic sodium (b) at a temperature from 100° C. to 500° C. in an inert gas atmosphere. The order in which the alkali metal-containing compound (a) and the metallic sodium (b) are mixed is not particularly limited.

Examples of the inert gas include helium, nitrogen, and argon.

The temperature when preparing the base composition is preferably from 100° C. to 500° C., more preferably from 110° C. to 300° C., and even more preferably from 120° C. to 280° C. When the temperature is from 100° C. to 500° C., the metallic sodium melts and therefore tends to be easily dispersed and mixed, and also tends to be sufficiently fired such that a highly active catalyst is formed.

The heating time when preparing the base composition is preferably from 10 minutes to 5 hours, more preferably from 30 minutes to 3 hours, and even more preferably from 30 minutes to 2 hours. When the heating time is from 10 minutes to 5 hours, firing is sufficiently implemented, and a highly active catalyst tends to be formed.

The alkaline earth metal-containing compound (c) may be added to the mixture of the alkali metal-containing compound (a) and the metallic sodium (b), and the order in which the alkali metal-containing compound (a), the metallic sodium (b), and the alkaline earth metal-containing compound (c) are mixed is not particularly limited.

Because the alkali metal-containing compound (a) and the alkaline earth metal-containing compound (c) are highly hygroscopic, a heat treatment may be performed before the preparation of the base composition. The heat treatment before preparation is preferably performed under an inert gas or vacuum conditions. The temperature of the heat treatment before preparation is not particularly limited as long as it is a temperature at which unnecessary moisture can be removed, and is normally from 200° C. to 500° C., and preferably from 250° C. to 400° C.

When the heat treatment temperature is set from 200° C. to 500° C., moisture in the compound can be sufficiently removed, and a highly active catalyst may be readily formed. The heat treatment time before preparation is preferably from 10 minutes to 5 hours, more preferably from 30 minutes to 3 hours, and even more preferably from 30 minutes to 2 hours. When the heating time is set to a range from 10 minutes to 5 hours, moisture can be sufficiently removed, and a highly active catalyst tends to be formed.

After the reaction is completed, the reaction solution and the base composition can be separated by an ordinary method such as fractional sedimentation, centrifugation, or filtration.

The base composition acts as a catalyst in the synthesis reaction of the compound represented by formula (1), but also functions as an irreversible reaction initiator. Thus, the amount of the base composition in the system decreases as the synthesis reaction of the amine compound proceeds. In addition, when a large amount of the base composition is added all at once, heat generation occurs, and side reactions may be promoted. Therefore, in the synthesis reaction of the compound represented by formula (1), the base composition is preferably divided in fractions and added two or more times. There is no particular upper limit to the number of times of fractional addition of the base composition, but practically, the number of times of the fractional addition is not more than 10 times, and may be not more than 5 times, or not more than 3 times. In particular, dividing the base composition into fractions and adding the base composition two or more times in fractions is beneficial when the synthesis reaction is carried out in a system not containing a solvent.

The base composition may also be introduced into the reaction solution continuously or intermittently at a constant rate. The time required for introduction is, for example, from 0.1 to 36 hours, preferably from 0.5 to 6 hours, and more preferably from 2 to 5 hours. The rate of introduction may be constant or may be varied over time.

In the production method of the present embodiment, a mass of the base composition is generally from 0.01 to 400 parts by mass, preferably from 0.1 to 300 parts by mass, and more preferably from 1.0 to 150 parts by mass, relative to 100 parts by mass of the compound represented by Formula (3). When the addition is divided into multiple fractions, a total amount of the base composition is preferably within the range described above.

A reaction temperature of the synthesis reaction of the compound represented by Formula (1) may be appropriately adjusted, and is generally in a range from 0 to 150° C., preferably from 10 to 120° C., more preferably from 10 to 40° C., and even more preferably from 10 to 35° C. A sufficient reaction rate may be achieved by setting the temperature to 0° C. or higher.

The synthesis reaction is preferably performed in an argon atmosphere.

In the production method according to the present embodiment, a solvent may be used, or production may be carried out without a solvent.

The solvent is appropriately selected according to the reaction temperature, the reaction product, and the like. When a solvent is used in the synthesis reaction described above, the formed reaction solution may be concentrated as necessary, after which the residue may be used as is as the compound represented by Formula (1) or as the amine composition. Alternatively, after an appropriate post-treatment is performed, the treated residue may be used as the compound represented by Formula (1) or as the amine composition. Specific examples of the method of the post-treatment include well-known purification methods, such as distillation and chromatography.

A filtration aid may be used to remove the base composition after completion of the reaction. Examples of the filtration aid include diatomaceous earth, aluminum hydroxide, hydrotalcite, magnesium silicate, magnesium oxide, and silicon oxide. Preferable examples include Kyowaad 600 (available from Kyowa Chemical Industry Co., Ltd.), Celite 503 (available from Imerys Filtration Minerals Inc.), Celite Hyflo Super-Cel (available from Imerys Filtration Minerals Inc.), and Celite Standard Super-Cel (available from Imerys Filtration Minerals Inc.), and Celite Standard Super-Cel is more preferable.

<Epoxy Resin Composition>

The compound represented by Formula (1) and the amine composition can also be used as a curing agent for an epoxy resin. That is, an epoxy resin curing agent according to the present embodiment preferably contains an amine compound or an amine composition according to the present embodiment. Moreover, the epoxy resin composition of the present embodiment preferably contains the epoxy resin curing agent described above and an epoxy resin.

The epoxy resin ordinarily has from 2 to 10 epoxy groups per molecule, preferably from 2 to 6 epoxy groups, more preferably from 2 to 4 epoxy groups, and even more preferably 2 epoxy groups per molecule. The epoxy group is preferably a glycidyl ether group. The epoxy resin may be a low molecular weight compound (for example, a number average molecular weight of less than 2000) or a high molecular weight compound (polymer, for example, a number average molecular weight of not less than 2000). The epoxy resin of the polymer may be an aliphatic compound, an alicyclic compound, or a compound having an aromatic ring. In particular, the epoxy resin preferably has, per molecule, two aromatic rings and/or two six-membered aliphatic rings, and more preferably has two aromatic rings per molecule. Among these, epoxy resins obtained through a reaction between epichlorohydrin and a compound having two or more reactive hydrogen atoms (for example, a polyol) are preferable. Specific examples of the raw materials of the epoxy resin include bisphenol A (2,2-bis(4-hydroxyphenyl)propane) or a hydride thereof, bisphenol F (4,4'-dihydroxydiphenylmethane), or a hydride thereof, tetrabromobisphenol A (2,2-bis(3,5-dibromo-4-hydroxyphenyl)propane) or a hydride thereof, a novolac resin in which cresol is reacted with formaldehyde, hexahydrophthalic acid, and the like. As the epoxy resin that can be used in the epoxy resin composition, in addition to the above, the disclosures of paragraphs [0036] to [0039] of JP 2018-083905 A, and paragraphs [0032] to [0035] of JP 2018-135433 A, the contents of which are incorporated herein, can be referenced.

A content of the epoxy resin in the epoxy resin composition is preferably not less than 60 mass %, and more preferably not less than 65 mass %, in the solid content not including the diluent. The upper limit is preferably not greater than 89 mass %, more preferably not greater than 87 mass %, and even more preferably not greater than 86 mass %.

One type of epoxy resin may be used, or a plurality of types may be used. When a plurality of epoxy resins are used, the total amount thereof is within the range described above.

The epoxy resin composition may include a curing agent besides the compound represented by Formula (1) and the amine composition. As such other curing agents, an amine-based curing agent described in paragraph [0029] of JP 6177331 B and an amine-based curing agent described in paragraphs [0011] to [0016] of JP 2011-213983 A, the contents of which are incorporated herein, can be referenced.

The epoxy resin composition may contain components besides the epoxy resin and curing agent. Specific examples of other components that may be contained include reactive diluents, non-reactive diluents, curing accelerators, plasticizers, pigments, dyes, fillers, release agents, toughening agents, antioxidants, UV absorbers, photostabilizers, fluidizers, leveling agents, defoaming agents, flame retardants, or thickeners.

A cured product according to the present embodiment is formed from the epoxy resin composition. The cured product can be used in a wide range of fields, such as in architectural paints, adhesives, automotive components, aircraft components, composite materials, printed circuit board materials, insulating impregnated materials of a heavy electrical machinery, and sealing materials for electronic devices. In addition, the cured product is preferably used in the applications described in paragraph [0045] of JP 2018-

083905 A, paragraph [0053] of JP 2018-135433 A, paragraph [0039] to [0043] of JP 2016-527384 T, and paragraph [0048] of JP 2011-213983 A, the contents of which are incorporated herein.

<Polyurethane Urea Resin Composition>

The amine compound represented by Formula (1) and the amine composition can be used as a curing agent for curing a urethane prepolymer. Furthermore, a polyurethane urea resin composition of the present embodiment preferably contains the urethane prepolymer curing agent above and a urethane prepolymer.

A cured product according to the present embodiment is formed from a polyurethane urea resin composition.

<Polyamide Varnish>

The compound represented by Formula (1) and the amine composition can be used for a polyamide varnish containing a compound having at least one carboxyl group. A polyamide, in which this polyamide varnish has been subjected to polycondensation, can be formed. The compound having a carboxyl group is preferably a dicarboxylic acid having two carboxyl groups.

EXAMPLES

The present invention will be described in further detail hereinafter using examples and comparative examples, but the present invention is not limited to the following examples.

<Analysis of Amine Compounds>
(1) Gas Chromatography (GC) Analysis

The content ratios of each component in the amine composition were measured through the following method using GC analysis.
Instrument: GC-2025 available from Shimadzu Corporation
  Column: CP-Sil 8 CB for Amines (0.25 μm×0.25 mm×30 m), available from Agilent Technologies, Inc.
  Column temperature: The temperature was maintained at 80° C. for two minutes, and then increased to 150° C. at a rate of 8° C./minute, maintained at 150° C. for five minutes, and subsequently increased to 300° C. at a rate of 15° C./minute, and then maintained at 300° C. for five minutes.
Solvent: 2-Propanol
(2) Gas Chromatography-Mass Spectrometry (GC-MS) Analysis For each component in the produced amine compound and amine composition, GC-MS analysis was employed to identify the structure by mass spectrometry as follows.
EI$^+$ Mode
Instrument: GC7890A available from Agilent Technologies, Inc.
  Column: DB-1MS (0.25 μm×0.25 mm×30 m), available from Agilent Technologies, Inc.
Carrier Gas: Helium
  Column temperature: The column temperature was maintained at 50° C. for two minutes, subsequently increased to 320° C. at a rate of 20° C./minute, and then maintained at 320° C. for ten minutes.
  Mass spectrometer: AccuTOF GCX, available from JEOL, Ltd.
  Ionization technique: Electron ionization method (EI$^+$)
  Ionization energy: 70 eV
  Ion source temperature: 250° C.
FI$^+$ Mode
Instrument: GC7890A available from Agilent Technologies, Inc.
  Column: DB-1MS (0.25 μm×0.25 mm×30 m), available from Agilent Technologies, Inc.
  Column temperature: The column temperature was maintained at 50° C. for two minutes, subsequently increased to 320° C. at a rate of 20° C./minute, and then maintained at 320° C. for ten minutes.
  Mass spectrometer: AccuTOF GCX, available from JEOL, Ltd.
  Ionization technique; Field ionization method (FI$^+$)

<Preparation of Base Composition>

In an argon atmosphere, a 200 mL round-bottom flask equipped with a magnetic stirrer was charged with 23.375 g of cesium carbonate ($Cs_2CO_3$, available from Fujifilm Wako Pure Chemical Corporation) which had been dried under reduced pressure at a temperature of 300° C., 1.65 g of metallic sodium (available from Fujifilm Wako Pure Chemical Corporation), and 17.6 g of magnesium oxide (MgO, available from Fujifilm Wako Pure Chemical Corporation) which had been dried under reduced pressure at a temperature of 300° C. The contents of the round-bottom flask were heated and stirred for one hour at 250° C. using an aluminum block heater/stirrer, followed by removal of the round-bottom flask from the aluminum block heater/stirrer. The contents were cooled to room temperature by air cooling, and thereby a base composition was obtained.

Example 1

In an argon atmosphere, a magnetic stirrer, 5.358 g of benzylamine (available from Tokyo Chemical Industry Co., Ltd.), and 3.080 g of 5-norbornene-2-methylamine (isomer mixture, available from Tokyo Chemical Industry Co., Ltd.) were charged into a 200 mL round-bottom flask, followed by addition of 0.996 g of the base composition. A reaction was initiated with stirring at 500 rpm in the argon atmosphere at 25° C. Additional amounts of the base composition were added to the mixture under an argon atmosphere at 60 minutes, 120 minutes, 180 minutes, and 240 minutes after the beginning of the reaction. The amount of each addition was 0.996 grams. After the passage of 360 minutes from the beginning of the reaction, the reaction was terminated by adding 16 mL of isopropyl alcohol.

To the resulting suspension, 50 mL of chloroform and 40 cm$^3$ of Celite Standard Super-Cel (available from Junsei Chemical Co., Ltd.) were added, and the mixture was suction filtered using filter paper No. 5C (available from Kiriyama Glass Works Co.), Kiriyama funnel SB-60 (60 mmφ, available from Kiriyama Glass Words Co.). 0.5M HCl and chloroform were added to the filtrate, and this mixture was subjected to liquid separation. Then, the aqueous phase was collected. Next, 1M sodium hydroxide and chloroform were added thereto once again and the resultant mixture was subjected to liquid separation, followed by collection of the organic phase. And subsequently the chloroform was distilled away under reduced pressure, and 8.1 g of an amine composition were obtained.

When the obtained amine composition was subjected to GC-MS analysis, it was found that the composition contained benzylamine and amine compounds a to e of the compositional formula $C_{15}H_{23}N_2$ represented by Formula (1-1) or (1-2). According to GC analysis, the conversion ratio of the benzylamine was 53%, the conversion ratio of aminomethyl norbornene was 86%, and the yield of the amine compounds a to e based on aminomethyl norbornene was 67%. From the obtained chromatograms, the retention times and the surface area ratios excluding the solvent of the amine compounds a to e, the aminomethyl norbornene, and the benzylamine were as follows.

Benzylamine (retention time: 4.50 min): 34.9%

Aminomethyl norbornene (retention time: 4.94 min and 5.03 min): 5.8%

Amine compound a (retention time: 21.38 min): 9.8%
Amine compound b (retention time: 21.52 min): 6.7%
Amine compound c (retention time: 21.77 min): 2.8%
Amine compound d (retention time: 21.90 min): 29.4%
Amine compound e (retention time: 21.96 min): 2.2%

[Chem. 12]

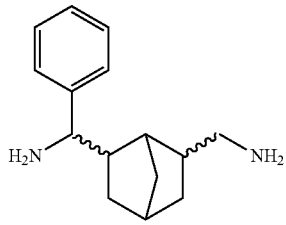

(1-1)

[Chem. 13]

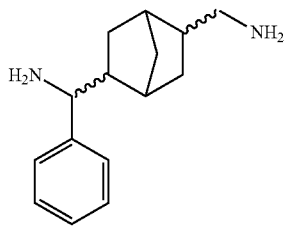

(1-2)

<Distillation Purification of Amine Composition>

An amount of 30.4 g of the amine composition obtained above was distilled at a vacuum pressure of 0.25 kPa, and the benzylamine was distilled off, after which an amine composition X containing, as main components, the amine compounds a to e represented by Formula (1-1) or (1-2) was collected as a fraction.

Furthermore, NMR measurements of the amine composition X found that a ratio of an area of a peak at chemical shifts 7.21 to 7.34 ppm, which corresponds to the aromatic hydrogens of the compound represented by Formula (1-1) and of the compound represented by Formula (1-2), to an area of a peak at chemical shifts 3.41 to 3.53 ppm, which corresponds to the hydrogen at the benzyl position, was 5 to 1. Thus, it was confirmed that a bond forming reaction occurred on the hydrogen at the benzyl position of the benzylamine used in the substrate.

<Preparation of an Epoxy Resin Composition>

An epoxy resin composition was prepared by mixing 0.930 g of a bisphenol A-type liquid epoxy resin (trade name; JER828, available from Mitsubishi Chemical Corporation, epoxy equivalent weight: 186 g/eq) and 0.288 g of the amine composition X obtained by distillation and purification.

<Preparation of an Epoxy Resin Cured Product>

An aluminum pan for differential scanning calorimetry (hereinafter, abbreviated as DSC) was filled with 10 mg of the epoxy resin composition prepared above. The temperature was raised from 30° C. to 280° C. in a DSC instrument under a nitrogen atmosphere at a ramp rate of 5° C./minute, the temperature was then maintained at 280° C. for 5 minutes, followed by rapid cooling at a rate of 20° C./minute.

<Measurement of Glass Transition Temperature of Epoxy Resin Cured Product>

The glass transition temperature (hereinafter, abbreviated as Tg) of the epoxy resin cured product obtained above was determined by differential scanning calorimetry using the "DSC6220" differential scanning calorimeter (available from Seiko Instruments Inc.) at temperatures from 30° C. to 250° C. with a ramp rate of 5° C./minute. The results indicated that the Tg of the epoxy resin cured product was 161.3° C.

The invention claimed is:

1. An amine composition which is a reaction product of a compound represented by Formula (2) and a compound represented by Formula (3), and contains a compound represented by Formula (1)

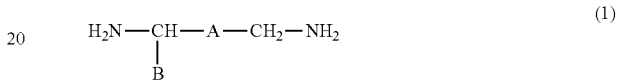

(1)

where A is a cyclic alkylene group, and B is a group selected from phenyl group, naphthyl group, anthracenyl group, phenanthrenyl group, biphenyl group, fluorenyl group, thienyl group, furyl group, pyridyl group, oxazol 1 group, pyrrolyl group, imidazolyl group, pyrazolyl group, indolyl group, and triazinyl group;

(2)

where E is a group selected from phenyl group; naphthyl group, anthracenyl group, phenanthrenyl group, biphenyl group, fluorenyl group, thienyl group, furyl group, pyridyl group, oxazolyl group, pyrrolyl group, imidazolyl group, pyrazolyl group, indolyl group, and triazinyl group;

(3)

where D is a cyclic alkenyl group.

2. The amine composition according to claim 1, wherein A in Formula (1) is a norbornane diyl group.

3. The amine composition according to claim 1, wherein B in Formula (1) is a phenyl group.

4. The amine composition according to claim 1, wherein E in Formula (2) is a phenyl group.

5. The amine composition according to claim 1, wherein B in Formula (1) is bonded to a methine group (CH) in Formula (1) without a linking group being interposed therebetween.

6. A method for producing an amine compound represented by Formula (1) or an amine composition comprising the compound represented by Formula (1), the method comprising:

reacting a compound represented by Formula (2) with a compound represented by Formula (3) in the presence of a base composition

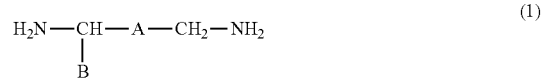

(1)

where A is a cyclic alkylene group, and B is a group selected from phenyl group, naphthyl group, anthracenyl group, phenanthrenyl group, biphenyl group, fluorenyl group, thienyl group, furyl group, pyridyl group, oxazolyl group, pyrrolyl group, imidazolyl group, pyrazolyl group, indolyl group, and triazinyl group;

  (2)

where E is a group selected from phenyl group, naphthyl group, anthracenyl group, phenanthrenyl group, biphenyl group, fluorenyl group, thienyl group, furyl group, pyridyl group, oxazolyl group, pyrrolyl group, imidazolyl group, pyrazolyl group, indolyl group, and triazinyl group;

  (3)

where D is a cyclic alkenyl group.

7. The production method according to claim 6, wherein the base composition comprises: a cesium-containing compound (a) selected from cesium carbonate and cesium hydroxide; and a metallic sodium (b).

8. The production method according to claim 6, wherein, in the reaction between the compound represented by Formula (2) and the compound represented by Formula (3), the base composition is added in fractions two or more times.

9. An amine compound represented by Formula (1)

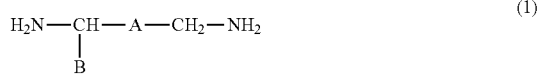  (1)

where A is a cyclic alkylene group, and B is a group selected from phenyl group, naphthyl group, anthracenyl group, phenanthrenyl group, biphenyl group, fluorenyl group, thienyl group, furyl group, pyridyl group, oxazolyl group, pyrrolyl group, imidazolyl group, pyrazolyl group, indolyl group, and triazinyl group.

10. The amine compound according to claim 9, wherein A in Formula (1) is a norbornane diyl group.

11. The amine compound according to claim 9, wherein B in Formula (1) is a phenyl group.

12. The amine compound according to claim 9, wherein B in Formula (1) is bonded to a methine group (CH) in Formula (1) without a linking group being interposed therebetween.

13. An epoxy resin curing agent comprising the amine compound of claim 9.

14. An epoxy resin composition comprising the epoxy resin curing agent of claim 13 and an epoxy resin.

15. A cured product formed from the epoxy resin composition of claim 14.

16. A curing agent of urethane prepolymer having a NCO group at a terminal, comprising the amine compound of claim 9.

17. A polyurethane urea resin composition comprising the curing agent of urethane prepolymer having a NCO group at a terminal of claim 16, and a urethane prepolymer having a NCO group at a terminal.

18. A cured product formed from the polyurethane urea resin composition of claim 17.

19. A polyamide varnish comprising the amine compound of claim 9 and a compound containing at least one carboxyl group.

20. A polyamide that is a polycondensate of the polyamide varnish of claim 19.

* * * * *

UNITED STATES PATENT AND TRADEMARK OFFICE
CERTIFICATE OF CORRECTION

PATENT NO. : 11,548,847 B2
APPLICATION NO. : 17/433134
DATED : January 10, 2023
INVENTOR(S) : Yuiga Asai It is certified that error appears in the above-identified patent and that said Letters Patent is hereby corrected as shown below:

In the Claims

Column 14, Line 27 (Claim 1, Line 11), please change "oxazol 1" to -- oxazolyl --.
Column 14, Line 32 (Claim 1, Line 14), please change "group;" to -- group, --.

Signed and Sealed this
Twenty-seventh Day of June, 2023

Katherine Kelly Vidal
*Director of the United States Patent and Trademark Office*